United States Patent [19]

Langer et al.

[11] Patent Number: 5,250,652
[45] Date of Patent: Oct. 5, 1993

[54] HIGH LOADING WATER-DISPERSIBLE UVA AND/OR UVB LIGHT-ABSORBING COPOLYMER

[75] Inventors: Matthew E. Langer, New City, N.Y.; Ferial Khorshahi, Leonia, N.J.

[73] Assignee: Lever Brothers Company, Division of Conopco, Inc., New York, N.Y.

[21] Appl. No.: 922,589

[22] Filed: Jul. 30, 1992

[51] Int. Cl.$^5$ .............................................. C08G 14/00
[52] U.S. Cl. .................................. 528/125; 528/128; 528/176; 528/183; 528/185; 528/189; 528/192; 528/193; 528/194; 528/220; 528/272; 528/288; 528/292; 528/302; 528/303; 528/304; 528/305; 528/308; 528/308.6; 528/332
[58] Field of Search ............... 528/125, 128, 176, 183, 528/185, 189, 192, 193, 194, 220, 272, 288, 292, 302, 303, 304, 305, 308, 308.6, 332

[56] References Cited

U.S. PATENT DOCUMENTS

| | | | |
|---|---|---|---|
| 3,864,473 | 2/1975 | Ciaudelli | 424/60 |
| 4,153,744 | 5/1979 | Remley | 427/160 |
| 4,324,684 | 4/1982 | Geiger et al. | 252/389.2 |
| 4,524,061 | 6/1985 | Cho et al. | 424/60 |
| 4,545,980 | 10/1985 | Hill | 424/60 |
| 4,743,632 | 5/1988 | Marinovic | 523/118 |
| 4,788,054 | 11/1988 | Bernhardt et al. | 424/59 |
| 4,839,160 | 6/1989 | Forestier et al. | 424/59 |

OTHER PUBLICATIONS

Ihara et al., *J. Polym. Sci., Part A-1*, 9(8):2413 (1971).

*Primary Examiner*—Samuel A. Acquah
*Attorney, Agent, or Firm*—Ronald A. Koatz

[57] ABSTRACT

The invention is concerned with novel water-dispersible copolymers which contain at least one UVA light-absorbing monomer, one UVB light-absorbing monomer, one hydrophilic monomer, and optionally one hydrophobic monomer component. The UVA light-absorbing monomer absorbs at λmax ultraviolet light in the 320–400 nm range. The UVB light-absorbing monomer absorbs at max ultraviolet light in the 290–320 nm range. Because of the $R_3$ group used in the invention, the copolymers of the invention permit higher loading of UV monomers than previously obtainable.

11 Claims, No Drawings

HIGH LOADING WATER-DISPERSIBLE UVA AND/OR UVB LIGHT-ABSORBING COPOLYMER

BACKGROUND OF THE INVENTION

1. Field of the Invention

The subject invention relates to novel copolymers which contain a UVA light-absorbing monomer and/or a UVB light-absorbing monomer; and a hydrophilic monomer component. The copolymers may optionally contain a hydrophobic monomer component. The copolyesters may be used in fabric care, skin care, and in other applications recognized by those skilled in the art.

2. Prior Art

The harmful effects of solar radiation are well known. The UVB (290–320 nm) portion of the solar spectrum is largely responsible for erythema (sunburn) and cancer (M. M. Rieger, Cosmet Toiletries, 102(3):91 (1987); C. Taylor, Skin Cancer Foundation J., 4:90 (1986)). The UVA (320–400 nm) portion of the solar spectrum is believed to be responsible for skin aging and premature wrinkling (L. H. Kligman, F. J. Akin, and A. M. Kligman, J. Invest. Dermatol., 84:272 (1985)).

In addition, UV light is also known to fade garments, especially in areas of high solar intensity This problem has been partially addressed via the application of various monomeric chromophores to garment surfaces (K. H. Remley U.S. Pat. No. 4,153,744; R. J. Bernhardt et al U.S. Pat. No. 4,788,054; P. C. Crews, et al., Text. Chem. Color, 11:21 (1987); B. Milligan et al., Polym. Deorad. Stab., 10(4):335 (1985)).

None of the above references relating to the protection of garments from solar radiation teach the use of polymeric UV light-absorbers.

Several references teach polymeric UV light-absorbers which selectively filter out either UVB or UVA light at maximum absorbance ($\lambda$max). None of these references, however, teach the use of either a hydrophobic or hydrophilic component to control the dispersibility and adsorption properties of the polymer. Further, with regard to the embodiment of the invention relating to copolymers with both UVA and UVB monomers (i.e., broad spectrum absorbency), none of these references teach copolymers with such broad spectrum absorbency.

Ciaudelli U.S. Pat. No. 3,864,473 teaches the use of 4-dimethylaminobenzoate-grafted poly(ethyleneimine) as a polymeric UV light absorber. The use of the aminobenzoate chromophore alone, however, limits the polymer's maximum absorbance to the UVB range. Moreover, the use of either a hydrophobic or hydrophilic component to control the dispersibility and adsorption properties of the polymer is not taught.

Cho et al. U.S. Pat. No. 4,524,061 teaches the use of poly(methacrylate) poly(vinylpyrrolidone) poly(vinyl 4-aminobenzoate) copolymer as a polymeric UV light absorber. The use of the aminobenzoate chromophore alone, however, limits the polymer's maximum absorbance to the UVB range. Moreover, the use of either a hydrophobic or hydrophilic component to control the dispersibility and adsorption properties of the polymer is not taught.

French Patent 2,617,399 to Lapoiriere et al. teaches the use of cinnamate-grafted poly(acrylamide) as a polymeric UV light absorber. The use of the cinnamate chromophore alone, however, limits the polymer's maximum absorbance to the UVB range. Moreover, the use of either a hydrophobic or hydrophilic component to control the dispersibility and adsorption properties of the polymer is not taught.

Hill U.S. Pat. No. 4,545,980 teaches the use cinnamate-grafted poly(dimethylsiloxanol) as a polymeric UV light absorber. The use of the cinnamate chromophore alone, however, limits the polymer's maximum absorbance to the UVB range. Moreover, the use of either a hydrophobic or hydrophilic component to control the dispersibility and adsorption properties of the polymer is not taught.

Japanese Patent 60,099,186 to Pola Chemical Industries, Ltd. teaches the use of poly(glycidol)/poly(4-glycidylaminobenzoate) copolymer as a polymeric UV light absorber. The use of the aminobenzoate chromophore alone, however, limits the polymer's maximum absorbance to the UVB range. Moreover, the use of either a hydrophobic or hydrophilic component to control the dispersibility and adsorption properties of the polymer is not taught.

B. Jacquet et al., Rev. Gen. Caoutch. Plast., 54(575):85 (1977) teach the use of poly(vinyl stearate)/poly(vinyl (4'-dimethylaminobenzoyloxy)acetate) copolymer as a polymeric UV light absorber. The use of the aminobenzoate chromophore alone, however, limits the polymer's maximum absorbance to the UVB range. Moreover, the use of either a hydrophobic or hydrophilic component to control the dispersibility and adsorption properties of the polymer is not taught.

German Patent 2,726,568 to Jacquet et al., teaches the use of cyanodiphenylacrylic acid-grafted poly(vinyl acetate) as a polymeric UV light absorber. The use of the cyanodiphenylacrylate chromophore alone, however, limits the polymer's maximum absorbance to the UVB range. Moreover, the use of either a hydrophobic or hydrophilic component to control the dispersibility and adsorption properties of the polymer is not taught.

Forestier et al. U.S. Pat. No. 4,839,160 teaches the use of benzylidenecamphor-grafted poly(acrylamide) as a polymeric sunscreen. The use of the benzylidenecamphor chromophore alone, however, limits the polymer's maximum absorbance to the UVA range. Moreover, the use of either a hydrophobic or hydrophilic component to control the dispersibility and adsorption properties of the polymer is not taught.

In the applicant's co-pending application filed Apr. 23, 1992 and titled "Water Dispersible Copolymer Containing UVA and UVB Light-Absorbing Monomers", there is taught a novel water-dispersible polymeric sunscreen based on repeating units of a UVA light-absorbing monomer, a UVB light-absorbing monomer, and a poly(alkylene glycol) such as poly(ethylene glycol) as a hydrophilic group. The addition of poly(ethylene glycol) was found to be necessary for dispersion of the polymer through an aqueous medium. However, due to its relatively high molecular weight, the poly(ethylene glycol) unit lowers the overall weight percent of the UVA and UVB light-absorbing moieties, thereby dramatically diluting their efficiency. That is, the weight percent of UVA and UVB light absorbing moiety in the water dispersible polymer when utilizing poly(ethyleneglycol) is limited to about 50% if one also wishes to maintain water dispersibility. By contrast, if the hydrophilic moiety is of substantially lower molecular weight, such as in the polymers of the subject invention, a UVA and/or UVB chromophore loading of up to 95%, and perhaps higher, may be achieved while still maintaining water dispersibility.

In addition, several references teach that hydroxyamino acids and diamino acids may be copolymerized with difunctional monomers to give polyamides and polyurethanes However, none of the references teach the copolymerization of lysine (or other low molecular weight hydrophilic group of the invention) with a UVA and/or UVB light-absorbing chromophore.

Y. Ihara et al., J. Polym. Sci., Part A-1, 9(8):2413 (1971) teach the copolymerization of lysine with terephthaloyl chloride, with 4,4'-diphenyldicarbonyl dichloride, and with 2,6-naphthalenedicarbonyl dichloride to give optically active polyamides useful for amino acid adsorption studies. The copolymerization of lysine, or other hydrophilic groups of the invention, with a UVA and/or UVB light-absorbing chromophore is neither taught nor suggested.

Lim et al. U.S. Pat. No. 4,324,684, teaches the copolymerization of lysine with terephthaloyl chloride to afford a polyamide membrane for encapsulating hemoglobin. The copolymerization of lysine, or other hydrophilic groups of the subject invention, with a UVA and/or UVB light-absorbing chromophore is neither taught nor suggested.

Marinovic U.S. Pat. No. 4,743,632 teaches the copolymerization of poly(butylene glycol), dicyclohexylmethane-4,4'-diisocyanate, and lysine, serine, or arginine to give polyetherurethanes useful as surgical adhesive sealants. The copolymerization of lysine, or other hydrophilic groups of the invention, with a UVA and/or UVB light-absorbing chromophore is neither taught nor suggested.

In each of the above-identified references, the polymers used differ from the copolymers of the subject invention, there is no teaching of the use of both a UVA and a UVB light-absorbing unit in conjunction with a low molecular weight (i.e., monomeric) hydrophilic unit to control dispersion properties, and there is no teaching of the use of a UVA light-absorbing unit, a UVB light-absorbing unit, a low molecular weight (i.e.,, monomeric) hydrophilic unit, and optionally a hydrophobic unit to control adsorbance capabilities of the resulting polymer.

Thus, there is a need in the art for novel copolymers comprising a UVB light-absorbing moiety and/or a UVA light-absorbing moiety, a low molecular weight (i.e., monomeric) hydrophilic moiety which allows for a high weight percentage of UVA and/or UVB moiety (i.e., loading of up to 95%) in the resulting polymer and further allows the polymer to be solvated in aqueous media, and optionally a hydrophobic moiety to fine-tune the polymer's ability to adhere to a desired surface.

SUMMARY OF THE INVENTION

The subject invention provides novel water dispersible or water soluble copolymers which contain at least one UVA light-absorbing moiety and/or one UVB light-absorbing moiety; one low molecular weight (i.e., monomeric) hydrophilic moiety, and optionally one hydrophobic moiety. The use of the low molecular weight hydrophilic moiety allows a loading of UVA and/or UVB moiety of up to about 95%. In theory loading can go even higher than this.

These novel copolymers may be used in fabric care, skin care, and in other applications recognized by those skilled in the art.

DETAILED DESCRIPTION OF THE INVENTION

This invention relates to novel water-dispersible copolymers which contain at least one UVA light-absorbing moiety, one UVB light-absorbing moiety, one low molecular weight (i.e., monomeric) hydrophilic moiety, and optionally one hydrophobic moiety. The optional hydrophobic moiety may be used to fine-tune the copolymer's ability to adsorb onto a desired surface. In addition the relatively low molecular weight of the hydrophilic component permits much higher loading of UVA and/or UVB moiety than previously believed possible.

More specifically, the copolymers of the invention are intended to absorb a broad spectrum of ultraviolet radiation (i.e., both UVA and UVB light) at maximum wavelength. In addition, the copolymers of the invention are intended to achieve a balance in water-solubility such that they are soluble enough to be able to deliver normally insoluble UVA and UVB monomers to a desired surface but sufficiently insoluble such that the UVA and UVB light absorbing polymer can adhere or adsorb onto the desired surface.

The novel copolymers of the subject invention may be used in fabric care, skin care, and in other applications recognized by those skilled in the art.

COMPOSITIONS

The novel copolymers of the invention may be used in fabric care compositions (i.e., cleansing or detergent compositions) such as in heavy duty liquid detergents (generally enzyme containing) or powdered detergents. Examples of liquid or powdered detergents are described in Aronson U.S. Pat. No. 4,959,179 (for liquid detergent compositions) and Oldenburg et al. U.S. Pat. No. 4,929,379 (for powdered detergent compositions), both of which are incorporated herein by reference.

Liquid detergent compositions may be built or unbuilt and may be aqueous or non-aqueous. The compositions generally comprise about 5%-70% by weight of a detergent active material and from 0% to 50% of a builder. The liquid detergent compositions of the invention may further comprise an amount of electrolyte (defined as any water-soluble salt) whose quantity depends on whether or not the composition is structured. By structured is meant the formation of a lamellar phase sufficient to endow solid suspending capability.

More particularly, while no electrolyte is required for a non-structured, non-suspending composition, at least 1%, more preferably at least 5% by weight and most preferably at least 15% by weight electrolyte is used. The formation of a lamellar phase can be detected by means well known to those skilled in the art.

The water-soluble electrolyte salt may be a detergency builder, such as the inorganic salt sodium tripolyphosphate or it may be a non-functional electrolyte such as sodium sulphate or chloride. Preferably, whatever builder is used in the composition comprises all or part of the electrolyte.

The liquid detergent composition generally further comprises enzymes such as proteases, lipases, amylases and cellulases which, when present, may be used in amounts from about 0.01 to 5% of the compositions. Stabilizers or stabilizer systems may be used in conjunction with enzymes and generally comprise from about 0.1 to 15% by weight of the composition.

The enzyme stabilization system may comprise calcium ion, boric acid, propylene glycol and/or short chain carboxylic acids. The composition preferably contains from about 0.01 to about 50, preferably from about 0.1 to about 30, more preferably from about 1 to about 20 millimoles of calcium ion per liter.

When calcium ion is used, the level of calcium ion should be selected so that there is always some minimum level available for the enzyme after allowing for complexation with builders, etc., in the composition. Any water-soluble calcium salt can be used as the source of calcium ion, including calcium chloride, calcium formate, calcium acetate and calcium propionate. A small amount of calcium ion, generally from about 0.05 to about 2.5 millimoles per liter, is often also present in the composition due to calcium in the enzyme slurry and formula water.

Another enzyme stabilizer which may be used is propionic acid or a propionic acid salt capable of forming propionic acid. When used, this stabilizer may be used in an amount from about 0.1% to about 15% by weight of the composition.

Another preferred enzyme stabilizer is polyols containing only carbon, hydrogen and oxygen atoms. They preferably contain from 2 to 6 carbon atoms and from 2 to 6 hydroxy groups. Examples include propylene glycol (especially 1,2-propane diol which is preferred), ethylene glycol, glycerol, sorbitol, mannitol and glucose. The polyol generally represents from about 0.5% to about 15%, preferably from about 1.0% to about 8% by weight of the composition.

The composition herein may also optionally contain from about 0.25% to about 5%, most preferably from about 0.5% to about 3% by weight of boric acid. The boric acid may be, but is preferably not, formed by a compound capable of forming boric acid in the composition. Boric acid is preferred, although other compounds such as boric oxide, borax and other alkali metal borates (e.g. sodium ortho-, meta- and pyroborate and sodium pentaborate) are suitable. Substituted boric acids (e.g., phenylboronic acid, butane boronic acid and a p-bromo phenylboronic acid) can also be used in place of boric acid.

One especially preferred stabilization system is a polyol in combination with boric acid. Preferably, the weight ratio of polyol to boric acid added is at least 1 to 1, more preferably at least about 1.3 to 1.

With regard to the detergent active, the detergent active material may be an alkali metal or alkanolamine soap or a 10 to 24 carbon atom fatty acid, including polymerized fatty acids, or an anionic, a nonionic, cationic, zwitterionic or amphoteric synthetic detergent material, or mixtures of any of these.

Examples of the anionic synthetic detergents are salts (including sodium, potassium, ammonium and substituted ammonium salts) such as mono-, di- and triethanolamine salts of 9 to 20 carbon alkylbenzenesulphonates, 8 to 22 carbon primary or secondary alkanesulphonates, 8 to 24 carbon olefinsulphonates, sulphonated polycarboxylic acids prepared by sulphonation of the pyrolyzed product of alkaline earth metal citrates, e.g., as described in British Patent specification, 1,082,179, 8 to 22 carbon alkylsulphates, 8 to 24 carbon alkylpolyglycol-ethersulphates, -carboxylates and -phosphates (containing up to 10 moles of ethylene oxide); further examples are described in "Surface Active Agents and Detergents" (vol. I and II) by Schwartz, Perry and Berch. Any suitable anionic may be used and the examples are not intended to be limiting in any way. Examples of nonionic synthetic detergents which may be used with the invention are the condensation products of ethylene oxide, propylene oxide and/or butylene oxide with 8 to 18 carbon alkylphenols, 8 to 18 carbon fatty acid amides; further examples of nonionics include tertiary amine oxides with 8 to 18 carbon alkyl chain and two 1 to 3 carbon alkyl chains. The above reference also describes further examples of nonionics.

The average number of moles of ethylene oxide and/or propylene oxide present in the above nonionics varies from 1-30; mixtures of various nonionics, including mixtures of nonionics with a lower and a higher degree of alkoxylation, may also be used.

Examples of cationic surfactants include, but are not limited to the quaternary ammonium compounds such as the monoalkyltrimethyl and dialkyldimethylammonium halides or $C_1$-$C_3$ alkyl sulfates salts (i.e., methyl or ethyl sulfates), alkyl pyridinium salts and substituted immidazolinium species. Still other useful agents are the primary, secondary and tertiary amines and the condensation products of fatty acids with an alkyl polyamine (e.g., bis(amidoamine).

Another class of cationics which are contemplated for use in the compositions of the invention are ester linked quaternary ammonium materials of the following formula:

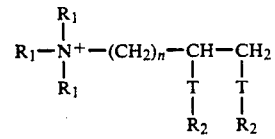

wherein each $R_1$ group is independently selected from $C_{1-4}$ alkyl, alkenyl or hydroxyalkyl groups; each $R_2$ group is independently selected from C12-24 alkyl or alkenyl groups;

T is

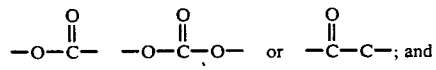

n is an integer from 0-5,

These ester-linked quaternary ammonium materials are particularly preferred for use in fabric conditioners because they are more biodegradable than conventional quaternary ammonium materials.

Examples of cationic surfactants include, but are not limited to the quaternary ammonium compounds such as the monoalkyltrimethyl and dialkyldimethylammonium halides or $C_1$-$C_3$ alkyl sulfate salts (i.e., methyl or ethyl sulfates), alkyl pyridinium salts and substituted immidazolinium species. Still other useful agents are the primary, secondary and tertiary amines and the condensation products of fatty acids with an alkyl polyamine (e.g., bis(amidoamine).

Examples of cationic detergents which may be used are the quaternary ammonium compounds such as alkyldimethylammonium halogenides.

Examples of amphoteric or zwitterionic detergents which may be used with the invention are N-alkylamine acids, sulphobetaines, condensation products of fatty acids with protein hydrolysates; but owing to their relatively high costs they are usually used in combination with an anionic or a nonionic detergent. Mixtures of the various types of active detergents may also be used, and preference is given to mixtures of an anionic and a nonionic detergent active. Soaps (in the form of their sodium, potassium and substituted ammonium salts) of fatty acids may also be used, preferably in conjunction with an anionic and/or nonionic synthetic detergent.

Builders which can be used according to this invention include conventional alkaline detergency builders, inorganic or organic, which can be used at levels from 0% to about 50% by weight of the composition, preferably from 1% to about 20% by weight, most preferably from 2% to about 8%.

Examples of suitable inorganic alkaline detergency builders are water-soluble alkalimetal phosphates, polyphosphates, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetracetates, nitrilotriacetates and N-(2-hydroxyethyl)-nitrilodiacetates; (2) water-soluble salts of phytic acid, e.g., sodium and potassium phytates (see U.S. Pat. No. No. 2,379,942); (3) water-soluble polyphosphonates, including specifically, sodium, potassium and lithium salts of ethane-1-hydroxy-1,1-diphosphonio acid; sodium, potassium and lithium salts of methylene diphosphonic acid; and sodium, potassium and lithium salts of ethane-1,1,2-triphosphonic acid. Other examples include the alkali methyl salts of ethane-2-carboxy-1,1-diphosphonic acid hydroxymethanediphosphonic acid, carboxylidiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water soluble salts of polycarboxylate polymers and copolymers as described in U.S. Pat. No. 3,308,067.

In addition, polycarboxylate builders can be used satisfactorily, including water-soluble salts of mellitic acid, citric acid, and carboxymethyloxysuccinic acid and salts of polymers of itaconic acid and maleic acid. Specific polycarboxylate builders include DPA (dipicolinic acid) and ODS (oxydisuccinic acid). Certain zeolites or aluminosilicates can be used. One such aluminosilicate which is useful in the compositions of the invention is an amorphous water-insoluble hydrated compound of the formula $Na_x(_yAlO_2.SiO_2)$, wherein x is a number from 1.0 to 1.2 and y is 1, said amorphous material being further characterized by a $Mg++$ exchange capacity of from about 50 mg eq. $CaCO_3$/g. and a particle diameter of from about 0.01 micron to about 5 microns. This ion exchange builder is more fully described in British Pat. No. 1,470,250.

A second water-insoluble synthetic aluminosilicate ion exchange material useful herein is crystalline in nature and has the formula $Na_z[(AlO_2)_y.(SiO_2)]xH_2O$, wherein z and y are integers of at least 6; the molar ratio of z and y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grams/gallon/minute/-gram. These synthetic aluminosilicates are more fully described in British Pat. No. 1,429,143.

In addition to the ingredients described hereinbefore, the preferred compositions herein frequently contain a series of optional ingredients which are used for the known functionality in conventional levels. While the detergent compositions are generally premised on aqueous, enzyme-containing detergent compositions, it is frequently desirable to use a phase regulant. This component together with water constitutes then the solvent matrix for the liquid compositions. Suitable phase regulants are well-known in liquid detergent technology and, for example, can be represented by hydrotropes such as salts of alkylarylsulfonates having up to 3 carbon atoms in the alkylgroup, e.g., sodium, potassium, ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 20%, the sum of phase regulant and water is normally in the range from 35% to 65%.

The preferred compositions herein can contain a series of further optional ingredients which are mostly used in additive levels, usually below about 5%. Examples of the like additives include: polyacids, suds regulants, opacifiers, antioxidants, bactericides, dyes, perfumes, brighteners and the like.

The beneficial utilization of the claimed compositions under various usage conditions can require the utilization of a suds regulant. While generally all detergent suds regulants can be utilized, preferred for use herein are alkylated polysiloxanes such as dimethylpolysiloxane, also frequently termed silicones. The silicones are frequently used in a level not exceeding 0.5%, most preferably between 0.01% and 0.2%.

It can also be desirable to utilize opacifiers inasmuch as they contribute to create a uniform appearance of the concentrated liquid detergent compositions. Examples of suitable opacifiers include: polystyrene commercially known as LYTRON 621 manufactured by Monsanto Chemical Corporation. The opacifiers are frequently used in an amount from 0.3% to 1.5%.

The compositions herein can also contain known antioxidants for their known utility, frequently radical scavengers in the art established levels, i.e., 0.001% to 0.25% (by reference to total composition). These antioxidants are frequently introduced in conjunction with fatty acids.

The liquid detergent compositions of the invention may also contain deflocculating polymers such as described in U.S. Pat. No. 5,071,586, hereby incorporated by reference.

When the liquid composition is an aqueous composition, the balance of the formulation consists of an aqueous medium. When it is in the form of a non-aqueous composition, the above ingredients make up for the whole formulation (a non-aqueous composition may contain up to 5% water).

An ideal liquid detergent composition might contain (all percentages by weight):
(1) 5-70% detergent active;
(2) 0-50% builder;
(3) 0-40% electrolyte
(4) 0.01-5% enzyme;
(5) 0.1-5% enzyme stabilizer;
(6) 0-20% phase regulant
(7) 0.01-5% copolymer of the invention; and (8) remainder water and minors The detergent composition of the invention might also be a powdered detergent composition.

Such powdered compositions generally comprise from about 5-40% of a detergent active system which generally consists of an anionic, a nonionic active, a fatty acid soap or mixtures thereof; from 20-70% of an alkaline buffering agent; up to about 40% builder and balance minors and water.

The alkaline buffering agent may be any such agent capable of providing a 1% product solution with a pH of above 11.5 or even 12. Advantageous alkaline buffering agents are the alkalimetal silicates, as they decrease the corrosion of metal parts in washing machines, and in particular sodium orthometa- or di-silicates, of which sodium metasilicate is preferred. The alkaline buffering agent is present in an amount of from 0 to 70% by weight, preferably from 0 to 30% by weight.

In addition the powdered detergent compositions of the invention can and normally will contain detergency builders in an amount of up to 40% by weight and preferably from 5 to 25% by weight of the total composition.

Suitable builders include sodium, potassium and ammonium or substituted ammonium pyro- and tri-polyphosphates, -ethylene diamine tetraacetates, -nitrilotriacetates, -etherpolycarboxylates, -citrates, -carbonates, -orthophosphates, -carboxymethyloxysuccinates, etc. Specific builders include DPA and ODS. Also less soluble builders may be included, such as e.g., an easily dispersible zeolite. Particularly preferred are the polyphosphate builder salts, nitrilotriacetates, citrates, carboxymethyloxysuccinates and mixtures thereof.

Other conventional materials may be present in minor amounts, provided they exhibit a good dissolving or dispersing behavior; for example sequestering agents, such as ethylenediamine tetraphosphonic acid; soil-suspending agents, such as sodiumcarboxymethylcellulose, polyvinylpyrrolidone or the maleic anhydride/vinylmethylether copolymer, hydrotropes; dyes; perfumes; optical brighteners; alkali-stable enzymes; germicides; anti-tarnishing agents; lather depressants; fabric softening agents; oxygen- or chlorine-liberating bleaches, such as dichlorocyanuric acid salts or alkalimetal hypochlorides.

The remainder of the composition is water.

A ideal powdered detergent composition might contain the following (all percentages by weight):

(1) 5-40% detergent active;
(2) 0-40% builder;
(3) 0-30% buffer salt;
(4) 0-30% sulfate;
(5) 0-20% bleach system;
(6) 0-4% enzyme;
(7) 0.01-5.0% copolymer of the invention; and
(8) Minors plus water to 100%

The UVA and UVB copolymers of the invention may also be used in personal product compositions such as, for example, soap bar compositions, facial or body cleansing compositions, shampoos for hair or body, conditioners, cosmetic compositions or sunscreen compositions.

In one embodiment of the invention, the copolymers of the invention may be used, for example, in a toilet bar (i.e., soap and/or detergent bar) formulation.

Typical toilet bar compositions are those comprising fatty acid soaps used in combination with a detergent other than fatty acid soap and free fatty acids. It should be noted that the composition may comprise no fatty acid soap and may be based on actives other than fatty acid soap. Mildness improving salts, such as alkali metal salt of isethionate, are also typically added. In addition other ingredients, such as germicides, perfumes, colorants, pigments, suds-boosting salts and anti-mushing agents may also be added.

Fatty acid soaps are typically alkali metal or alkanol ammonium salts of aliphatic alkane or alkene monocarboxylic acids. Sodium, potassium, mono-, di- and triethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 12 to about 18 carbons.

Examples of soap which may be used may be found in U.S. Caswell et al. Pat. No. 4,695,395 and Barrett U.S. Pat. No. 4,260,507, both of which are incorporated herein by reference.

In a soap-based bar, fatty acid soaps will generally comprise greater than 25% of the composition, generally from 30-95%. Preferably, the amount of soap will range from 40% to 70% by weight of the composition. In a bar-based on other actives, soap may comprise 0-50% by weight. In general, $C_8$ to $C_{24}$ fatty acid comprises 5-60% of the composition.

The compositions will also generally comprise a non-soap detergent which is generally chosen from anionic, nonionic, cationic, zwitterionic or amphoteric synthetic detergent materials or mixtures thereof. These surfactants are all well known in the art and are described, for example, in U.S. Pat. Nos. 4,695,395 and 4,260,507 discussed above. One preferred non-soap anionic is a $C_8$-$C_{22}$ acyl isethionate. These esters may be prepared by the reaction between alkali metal isethionate and mixed aliphatic fatty acids having from 8 to 22 carbons. The non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 15% of the compositions.

A preferred mildness improving salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betaine compounds or ether sulphates. These also may be present at 0.1 to 50% of the composition, preferably 0.5% to 25%.

The sulfate ester surfactant may comprise 0.01 to 45% by weight of the composition (as the monoester), preferably 25% to 40%, and 0.01% to 10% of the composition (as the diester), preferably 0.01% to 5%.

Other optional ingredients which may be present in soap bar compositions are moisturizers such as glycerin, propylene glycol, sorbitol, polyethylene glycol, ethoxylated or methoxylated ether of methyl glucose etc; water-soluble polymers such as collagens, modified celluloses (such as Polymer JR(®)), guar gums and polyacrylates; sequestering agents such as citrate, and emoients such as silicones or mineral oil. Another useful set of ingredients are various co-surfactants and non-soap detergents.

In a second embodiment of the invention, the copolymers of the invention may be present in a facial or body cleansing composition. Examples of such cleaning compositions are described, for example, in Small et al. U.S. Pat. No. 4,812,253 and Fujisawa U.S. Pat. No. 4,526,710, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener (e.g. magnesium aluminum silicate, Carbopol), conditioners, water soluble polymers (e.g. carboxymethyl cellulose), dyes, hydrotropes, brighteners, perfumes and germicides.

The fatty acid soaps used are such as those described above in uses in toilet bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695,395 mentioned above, or in Inman et al U.S. Pat. No. 4,854,333, hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

Preferred moisturizers are coco and tallow fatty acids. Some other preferred moisturizers are the nonocclusive liquid water soluble polyols and the essential amino acid compounds found naturally in the skin.

Other preferred nonocclusive moisturizers are compounds found to be naturally occurring in the stratum corneum of the skin, such as sodium pyrrolidone carboxylate, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—a Critical Evaluation," by J. Mausner, Cosmetics & Toiletries, May 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co, Inc.; Jaguar C-14-S made by Stein Hall; Mirapol A15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. A preferred nonionic hydroxypropyl guar gum material is Jaguar(®) HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1-5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok ®300 and 400 made by Staley, Inc.

A more complete list of cationic polymers useful in this embodiment of the invention is described in U.S. Pat. No. 4,438,095, issued Mar. 20, 1984, hereby incorporated by reference. Some of the more preferred cationics are listed in Col. 3, Section 2; Col. 5, section 8; Col. 8, section 10; and Col. 9, lines 10–15 of the Grollier/allec patent, incorporated herein by reference.

In a third embodiment of the invention, the UVA plus UVB copolymers of the invention may be used, for example, in a shampoo. Examples of such compositions are described in Inman U.S. Pat. No. 4,854,333, and Fujisawa U.S. Pat. No. 4,526,710, both of which are hereby incorporated by reference.

The shampoo compositions which may be used typically comprise a surfactant selected from any one of a wide variety of surfactants known in the art (such as those described in U.S. Pat. No. 4,854,333, incorporated herein by reference). The shampoo compositions may additionally comprise a compound considered useful for treating dandruff, e.g. selenium sulfide.

The compositions all may also optionally comprise a suspending agent, for example, any of several acyl derivative materials or mixtures thereof. Among these are ethylene glycol esters of fatty acids having 16 to 22 carbons. Preferred suspending agents include ethylene glycol stearates, both mono- and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another agent used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. Supplemental information on these agents is found in Whistler, Roy L. (Editor), *Industrial Gums—Polysaccharides and Their Derivatives* New York: Academic Press, 1973. Kelco, a Division of Merck & Co., Inc., offers xanthan gum as Keltrol(®).

A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R.T. Vanderbilt Company, Inc. Mixtures of suspending agents are also suitable for use in the compositions of this invention.

Other useful thickening agents are the cross-linked polyacrylates such as those manufactured by B.F. Goodrich and sold under the Carbopol(®) tradename.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials.

Other materials include alginates, polyacrylic acids, polyethylene glycol and starches, among many others. The nonionic polymers are discussed in detail in *Industrial Gums*, edited by Roy L. Whistler, Academic Press, Inc., 1973, and *Handbook of Water-Soluble Gums and Resins*, edited by Robert L. Davidson, McGraw-Hill, Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylaryl siloxane or a polyether siloxane copolymer and is present at a level of from about 0.1% to about 10.0% preferably from about 0.5% to about 5.0%. Mixtures of these fluids may also be used and are preferred in certain executions. The dispersed silicone particles should also be insoluble in the shampoo matrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, Jul. 20, 1970. Preferably the viscosity of these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in Geen U.S. Pat. No. 2,826,551; Drakoff U.S. Pat. No. 3,946,500, Jun. 22, 1976; Pader U.S. Pat. No. 4,364,837; and British Patent 849,433, Woolston. All of these patents are incorporated herein by reference. Also incorporated herein by reference is Silicon Compounds, distributed by Petrarch Systems, Inc., 1984. This reference provides a very good listing of suitable silicone materials.

Another silicone material useful is silicone gum. Silicone gums are described by Petrarch and others including Spitzer et al. U.S. Pat. No. 4,152,416, May 1, 1979, and Noll, *Chemistry and Technology of Silicones*, New York, Academic Press, 1968. Useful silicone gums are also described in General Electric Silicone Rubber Product Data Sheets SE 30, SE 33, SE 54 and SE 76. all of these references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane)(methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BASF Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.1% to about 10%, preferably from about 0.5% to about 5.0%, of the composition.

A typical shampoo composition may comprise (percentages by weight):
(1) 0.01-40% active;
(2) 0-5% lauramide MEA;
(3) 0-5% thickener;
(4) 0-2% fragrance;
(5) 0-1% preservative;
(6) 0.01-5% polymer of the invention; and
(7) remainder water.

In a fourth embodiment of the invention, the copolymer of the invention may be used in a conditioner composition such as is taught and described in Caswell et al. U.S. Pat. No. 4,913,828 which is hereby incorporated by reference.

More particularly, conditioner compositions are those containing a conditioning agent (e.g. alkylamine compounds) such as those described in U.S. Pat. No. 4,913,828.

In a fifth embodiment of the invention, the copolymer may be used in a cosmetic composition, such as is taught and is described in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymers such as carboxy vinyl polymers, for example, Carbomer 940 and 941; nonionic cellulose materials, such as methyl cellulose and hydroxy propyl methyl cellulose; cationic cellulose materials, such as Polymer JR 400; cationic gum materials, such as Jaguar C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid, 2-bromo-2-nitropropane-1,3-diol, phenoxyethanol, dibromodicyanobutane, formalin and Triclosan. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, a sufficient amount should be incorporated in the composition according to the invention to reduce the water activity from 1 to <0.9, preferably to <0.85 and most preferably <0.8, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1,3 diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, Fuller's Earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sun-screening agents, such as those described in Deckner et al. U.S. Pat. No. 4,919,934 hereby incorporated by reference, may also be used in the cosmetic compositions of the invention.

Such agents include, for example, p-aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphthloic acid and its salts, hydroxy diphenylsulfonates, coumarin derivatives, diazoles, quinine salts, quinoline derivatives, hydroxy or methoxy substituted benzophenones, uric or vilouric acid, tannic acid and its derivatives, hydroquinone, and benzophenones.

In a sixth embodiment of the invention, the copolymer of the invention may be used in a light duty liquid detergent composition such as those taught in Lamb et al. U.S. Pat. No. 4,671,894 Aronson et al. U.S. Pat. No. 4,368,146 and Bissett et al. U.S. Pat. No. 4,555,366, all of which are hereby incorporated by reference into the subject application.

Generally such compositions comprise a mixture of sulphate and sulphonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance.

Among other ingredients which may also be used in such compositions are opacifiers (e.g. ethylene glycol distearate), thickeners (e.g., guar gum), antibacterial agents, anti-tarnish agents, heavy metal chelators (e.g. ETDA), perfumes and dyes.

In a seventh and preferred embodiment of the invention, the copolymers of the invention are sunscreen agents used in a sunscreen composition.

Such sunscreen compositions, are preferably oil-in-water emulsions, wherein the emulsion is composed of an internal oil phase dispersed as spherical droplets in the external water phase. An emulsifier (surfactant or polymer) is used to stabilize the droplets against phase separation.

Such oil-in-water emulsions generally comprise:

(1) 1-30% of the polymer of the invention as the sunscreen agent. Other sunscreen agents which are well known in the art may be used in combination with the polymers. These include alkyl amino benzoates such as octyl p-dimethyl amino-benzoate (Padimate O), PABA, and cinnamates (e.g., ethylhexyl p-methoxy cinnamate);

(2) 0.5 to 10% anionic or nonionic emulsifier selected from the following groups: soaps, fatty acid amides, ethoxylated fatty acids, ethoxylated esters, ethoxylated ethers, ethoxylated alcohols, phosphated esters, polyoxyethylene fatty ether phosphates and acyl lactylates. These are used alone or in combination, preferably between 2 and 6%;

(3) 0 to 10% film forming polymer to provide wash resistance. In order to maintain the desired sun protection factor during use, the sunscreen must not be washed off. Film forming copolymers such as copolymers of PVP (i.e., eicosene-vinyl pyrrolidone copolymer, Ganex V-220 ex. GAF) and ethylene-vinyl acetate copolymers (AC-400A ex Allied-Signal) may be used;

(4) 1-30% oil soluble emollients such as lanolin, isopropyl myristate, glycerol stearate, cetyl alcohol, and dimethicone;

(5) 45-90% water;

0.05 to 5% of a polymeric thickener to provide an acceptable viscosity. Synthetic polymers (cross-linked acrylic acid polymer) or natural polymers such as modified cellulosics (hydroxy ethyl cellulose) or nonionic gums (guar, xanthan, or arabic) may be used;

(7) Optional ingredients include suspended particulate matter such as titanium dioxide, zinc oxide, talc, or kaolin, fragrances, and preservatives.

These compositions are prepared by pre-blending the oil phase of emollients, oil soluble polymers and surfactant (i.e., fatty acid) at 70°-° C. The oil phase is added to the pre-blend of the water phase (maintained at 70°-95° C.) and mixed until homogeneous. The mixture is cooled to 65° C. and the saponifying agent for the fatty acid is added. The emulsion is cooled to 50° C. and fragrance and preservatives added.

Two examples of typical sunscreen compositions are shown below:

| I | |
|---|---|
| Ingredient | Weight Percent |
| Water | 40.08 |
| Sunscreens | 16.00 |
| Petrolatum | 35.00 |
| Brij 721 (ex ICI)[a] | 1.16 |
| Brij 72 (ex ICI)[b] | 3.86 |
| Silicone Oil | 3.00 |
| Carbopol 934 (ex Goodrich)[c] | 0.40 |
| Sodium Hydroxide | 0.40 |
| Preservative | 0.10 |

[a]Steareth 21 (stearyl alcohol ethoxylated with 21 moles of ethylene oxide)
[b]Steareth 2 (stearyl alcohol ethoxylated with 2 moles of ethylene oxide)
[c]Cross-linked polyacrylic acid

| II | |
|---|---|
| Ingredient | Weight Percent |
| Water | 53.80 |
| Sunscreens | 16.00 |
| Eicosene-PVP copolymer | 3.00 |
| Isostearic Acid | 5.00 |
| ammonium Hydroxide | 0.40 |

| Ingredient | Weight Percent |
|---|---|
| II | |
| Glycerol Stearate | 2.25 |
| Cetyl Alcohol | 4.00 |
| Isopropyl Myristate | 3.00 |
| Lanolin | 0.10 |
| Carbomer 941 (ex Goodrich)[d] | 0.15 |
| Xanthan Gum | 0.20 |
| Preservative | 0.10 |

[d]Cross-linked polyacrylic acid

A third example of a sunscreen composition is also shown below:

| Ingredient | Weight Percent |
|---|---|
| III | |
| Polymer of Invention | 10.00 |
| Finsolv TN[e] | 10.00 |
| Stearic acid | 4.00 |
| Amphisol[f] | 3.00 |
| Cetyl alcohol | 1.50 |
| Water | 69.95 |
| Carbopol 980[g] | 0.15 |
| Triethanolamine | 1.00 |
| Methylparaben | 0.30 |
| Propylparaben | 0.10 |

[e]Benzoic acid ester of $C_{12}$-$C_{15}$ alcohol
[f]Cocamidobetaine
[g]Cross-linked polyacrylic acid The UV polymers of the invention may also be used in other products such as water-in-oil emulsions, creams, polymer gels, and sunscreen oils.

In an eighth embodiment of the invention, the molecule of the invention may be used in underarm deodorant/antiperspirant compositions such as those taught in Deckner U.S. Pat. No. 4,919,934, McCall U.S. Pat. No. 4,944,937 and Patini U.S. Pat. No. 4,944,938, all of which patents are hereby incorporated by reference.

Such compositions generally comprise a cosmetic stick (gel or wax) composition which in turn generally comprises one or more liquid base materials (e.g., water, fatty acid and fatty alcohol esters, water-insoluble ethers and alcohols, polyorganosiloxanes); a solidifying agent for solidifying the liquid base; and an active component such as bacteriostats or fungistats (for anti-deodorant activity) or astringent metallic salts (for antiperspirant activity).

These compositions may also comprise hardeners, strengtheners, emollients, colorants, perfumes, emulsifiers and fillers.

While various compositions are described above, these should not be understood to be limiting as to what other personal product compositions may be used since other compositions which may be known to those of ordinary skill in the art are also contemplated by this invention.

Copolymers

The copolymers of the invention may be defined by the following formula I:

$$-(A)_n-(B)_m-(C)_p-(D)_q- \quad (I)$$

wherein A is a moiety capable of absorbing UVA [320–400 nanometer (nm)] light at λmax and bearing the appropriate bifunctionality for copolymerization into the polymer main chain. Examples of such groups include planar aromatic moieties such as tertrahydroxybenzophenones; dicarboxydihydroxybenzophenones and alkane ester or acid halide derivatives thereof; dihydroxy-, dicarboxy-, and hydroxycarboxydibenzoylmethanes and alkane ester or acid halide derivatives thereof; dihydroxy-, dicarboxy-, and hydroxyce-boxystilbenes and alkane ester or acid halide derivatives thereof; bis(hydroxystyrenyl)benzenes; bis(carboxystyrenyl)benzenes and alkane ester or acid halide derivatives thereof; dihydroxy-, dicarboxy, and hydroxycarboxycarotenes and alkane ester or acid halide derivatives thereof; and any suitably functionalized species capable of copolymerization within the polymer chain and in accordance with the Woodward-Fieser, Fieser-Kuhn, and Nielsen Rules capable of absorbing ultraviolet light in the 320–400 nm range;

B is a moiety capable of absorbing UVB [320–400 nanometer (nm)] light λmax and bearing the appropriate bifunctionality for copolymerization into the polymer main chain. Examples of such groups include planar aromatic moieties such as 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; and other suitably functionalized species capable of copolymerization within the polymer chain and in accordance with the Woodward-Fieser, Fieser-Kuhn, and Nielsen Rules (D. L. Pavia, G. M. Lampman, and G. S. Kriz, Jr. "Introduction to Spectroscopy: A Guide for Students of Organic Chemistry," Saunders College Publishing, 1979, Philadelphia) capable of absorbing ultraviolet light in the 290–320 nm range;

C is a hydrophilic moiety incorporated to confer hydrophilicity to solvate the copolymer in aqueous media;

D is an optional hydrophobic moiety incorporated to adjust the water-solubility or water-dispersibility and binding strength to hydrophobic surfaces;

n may range from 0 to 250, preferably 50 to 250, and most preferably 150–250 except that n must be at least 1 if m is 0.

m may range from 0 to 250, preferably 50 to 250 except m must be at least 1 if n is 0;

p is at least 5 and may range from 5 to 500; and q may be zero and may range from 0 to 250.

It should be noted that if A and B are water soluble, then q (defining the chain length of the hydrophobic monomer) should be at least 1 to ensure deposition of the copolymer onto the desired surface. In addition, if the length of the hydrophilic moiety (defined as C) or the percentage of C as the total percentage of the copolymer is such that the resulting copolymer is too water soluble to effectively adsorb onto the desired surface (i.e., the copolymer preferentially remains in the aqueous vehicle), then q must be greater than 0 and large enough to ensure that adsorption takes place while at the same time not so large as to preclude water solubility or dispersibility.

In general, the level of p is chosen to balance the water solubility or dispersibility of the copolymer with its ability to adsorb onto a desired surface. In practice, a minimum value for p of approximately 10 is useful.

The UVA light-absorbing moiety A may comprise 0 to 99.9 mol % of the copolymer, preferably 10 to 80 mol %, and most preferably 25 to 75 mol %; the UVB light-absorbing moiety B may comprise 0 to 99.9 mol % of the copolymer, preferably 10 to 80 mol %, and most preferably 25 to 75 mol %; the hydrophilic moiety C may comprise 0.5 to 49.9 mol % of the copolymer, preferably 10 to 50 mol %, and most preferably 20 to 40 mol %; and the hydrophobic moiety, if present, may comprise 0.05 to 49.9 mol % of the copolymer. UVA or UVB must comprise at least 1%.

Although A, B, C, and D are expressed above as a block copolymer, it is to be understood that the places of A, B, C, and D may be interchanged in random order.

The copolymers of the subject invention may be further defined by the following formula II:

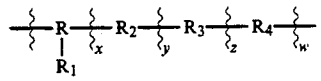

wherein:

R is a difunctional aryl or alkyl group such as for example, difunctional benzene or napththalene, preferably difunctional benzene or a difunctional straight or branched alkyl chain containing 4 to 16 carbon atoms;

$R_1$ is hydrogen or an aliphatic group having 1 to 20 carbons, preferably a straight-chained alkyl group having 1 to 12 carbons, most preferably 1 to 5 carbons, an aryl, an alkaryl, a secondary amine such as, for example, dialkylamine, an alkali metal sulfonate, an alkali metal carboxylate, and alkyl ether, or a halogen atom;

$R_2$ is a UVA light-absorbing moiety bearing the appropriate bifunctionality for incorporation into the main chain of the polymer. By bifunctional is meant any UVA light-absorbing monomer as defined above bearing at least the functional groups such as are well known to those skilled in the art. Examples include amines, alkyl esters, carboxylic acids, carboxylic acid halides, hydroxyl groups, etc;

$R_3$ is a carboxylate salt or sulfonate salt (wherein the counter ion is a metal or ammonium cation), or a quaternary ammonium derivative possessing the appropriate bifunctionality for incorporation into the main chain of the polymer. By bifunctional is meant any carboxylic acid, sulfonic acid or metal or amine salt derivative thereof, or any quaternary ammonium derivative bearing at least the functional groups such as are well known to those skilled in the art. Examples include amines, alkyl esters, carboxylic acids, carboxylic acid halides, hydroxyl groups, etc.

$R_4$ is a UVB light-absorbing moiety bearing the appropriate bifunctionality for incorporation into the main chain of the polymer. By bifunctional is meant any UVB light-absorbing monomer as defined above bearing at least the functional groups such are well known to those skilled in the art. Examples include amines, alkyl esters, carboxylic acids, carboxylic acid halides, hydroxyl groups, etc.

x, which represents the number of monomeric units of the optional hydrophobic group, is selected such that the hydrophobe is present at 0 to 49.9 mol % of the polymer;

y is selected such that the $R_2$ group is present at 0 to 99.9 mol % of the polymer (y must be greater than 0 if w is zero);

z is selected such that the $R_3$ group is present at 0.5 to 49.9 mol % of the polymer; and w is selected such that the $R_4$ group is present at 0 to 99.9 mol % of the polymer (w must be greater than 0 if y is zero).

As discussed above, the UVA and UVB light-absorbing monomers (as represented above by $R_2$ and $R_4$) are moieties bearing the appropriate bifunctionality for incorporation into the main chain of the polymer. The UVA light-absorbing monomer should absorb at its λmax ultraviolet light between 320 and 400 nm. The UVB light-absorbing monomer should absorb at its λmax ultraviolet light between 290 and 320 nm. λmax is defined as the wavelength of maximum absorbance as defined by the Beer-Lambert equation, $\epsilon = A/cl$, where $\epsilon$ = molar extinction coefficient, A = absorbance, c = molar concentration, and l = path length). Preferred monomers are either highly conjugated and/or poly(ene)-based derivatives and/or aromatic-based derivatives bearing the appropriate difunctional group.

Examples of such UVA absorbers which may be used include tetrahydroxybenzophenones, dihydroxydibenzoylmethanes, dicarboxydibenzoylmethanes and alkane ester or acid halide derivatives thereof, dihydroxystilbenes, dicarboxystilbenes and alkane ester or acid halide derivatives thereof, bis(hydroxystyrenyl)benzenes, and bis(carboxystyrenyl)benzenes and alkane ester or acid halide derivatives thereof. Preferred UVA light-absorbers are 2,2',4,4'-tetrahydroxybenzophenone, 4,4'-bis(carbomethoxy)stilbene, and 4,4'-stilbenedicarbonoyl dichloride for their efficient absorbance, commercial availability, and ease of preparation.

Examples of such UVB absorbers which may be used include 4-aminobenzoic acid esters, anthranilic acid esters, salicylate esters, hydroxycinnamate esters, dihydroxybenzophenones, dicarboxybenzophenones and alkane ester or acid halide derivatives thereof, dihydroxychalcones, and dicarboxychalcones and alkane ester or acid halide derivatives thereof. Preferred UVB light-absorbers are methyl 4-aminobenzoate, methyl 4-hydroxycinnamate, and 4,4'-dihydroxybenzophenone for their efficient absorbance, commercial availability, and ease of preparation.

Still other examples of UVA and UVB light-absorbing monomers which can suitably be used or functionalized prior to use by those skilled in the art may be found in Shaath, N. A., Encyclopedia of UV Absorbers for Sunscreen Products. Cosmetics and Toiletries, 1987, March (pp 21–39).

As discussed above, the UVA light-absorbing monomer may be added as 0 to 99.9 mol % of the polymer, preferably 10 to 80 mol %, and most preferably 25 to 75 mol %. The UVB light-absorbing monomer may be added as 0 to 99.9 mol % of the polymer, preferably 10 to 80 mol %, and most preferably 25 to 75 mol %. At least 1% of UVA or UVB monomer must be present.

The hydrophilic component (represented by $R_3$) is incorporated to confer hydrophilicity to naturally hydrophobic surfaces such as soiled cotton or polyester as well as to facilitate transfer of the polymer through an aqueous medium. Hydrophilic monomers which may be used include, but are not limited to the metal or ammonium salts of diamino acids such as arginine and lysine; thioamino acids such as cysteine; hydroxyamino acids such as hydroxylysine, hydroxyproline, and serine; hydroxyphenyl aminoacids such as tyrosine; dihydroxy acids such as glyceric acid and dihydroxybenzoic acid; and quaternary ammonium derivatives such as 1-trimethylammonium-2,3-dihydroxypropane chloride. The amino acids may be employed either as the free base or acid salt, and converted to the metal or ammonium salt thereof via treatment with the basic polymerization catalyst (infra) in situ.

In a preferred embodiment of the invention, $R_3$ is lysine sodium salt. The lysine sodium salt unit must be present in at least sufficient quantity to ensure that the final copolymer may be delivered throughout an aqueous medium. In general, this monomer is present as 1 to 50 mol %, preferably 2 to 20 mol % of the reaction mixture.

The hydrophobic monomer which may be optionally incorporated is used to adjust the water solubility and binding strength of the copolymer to hydrophobic surfaces. Suitable hydrophobic monomers which may be used include long chain aliphatic $\alpha,\omega$-diols, $\alpha,\omega$-diamines, or $\alpha,\omega$-dicarboxylic acids or diester or diacid chloride derivatives thereof. Another suitable class of hydrophobic monomers includes the aromatic 4,4'-phenylenediols, 4,4'-biphenols, or 4,4'-dihydroxydiphenyl ethers, as well as the analogous diamino or dicarboxylic acid, dicarboxylic acid diester, or dicarboxylic diacid chloride species. Especially preferred monomers are terephthalic acid or hexanedioic acid derivatives. These monomers may be added as 0 to 49.9 mol % of the reaction mixture, preferably 0 to 20 mol %.

In an especially preferred embodiment of the invention, the UVA light-absorbing monomer is 4,4'-stilbenedicarbonyl dichloride chloride; the UVB light-absorbing monomer is 4,4'-dihydroxybenzophenone, and the hydrophilic monomer is lysine sodium salt. The optional hydrophobic monomer is omitted completely.

The ratio of monomers can vary broadly depending upon the end use requirement such as whether the polymer is being used for UV light screening, soil release, anti-redeposition, or enzyme stabilization. However, in the especially preferred embodiment of the subject invention, the ratio of the UVA light-absorbing monomer to the mixture of the UVB light-absorbing monomer and the hydrophilic monomer may range from 1.2:1.0 to 1.0 to 1.2, preferably 1.1:1.0 to 1.0 to 1.1, and most preferably from 1.0:1.0. The ratio of UVB light-absorbing monomer to the hydrophilic monomer may range from 9:1 to 1:9, preferably 9:1 to 1:1 and most preferably 9:1 to 3:1.

However, as is usual for aqueously delivered adsorbants, some balance is generally sought between hydrophilic and hydrophobic properties. These can be fine tuned by those skilled in the art.

As mentioned above, in one preferred embodiment of the invention, the copolymers of the present invention may be based upon the condensation product of 4,4'-stilbenedicarbonyl dichloride, 4,4'-dihydroxybenzophenone, and lysine sodium salt.

These components may be combined via a 1-step transesterification reaction as set forth in Scheme 1:

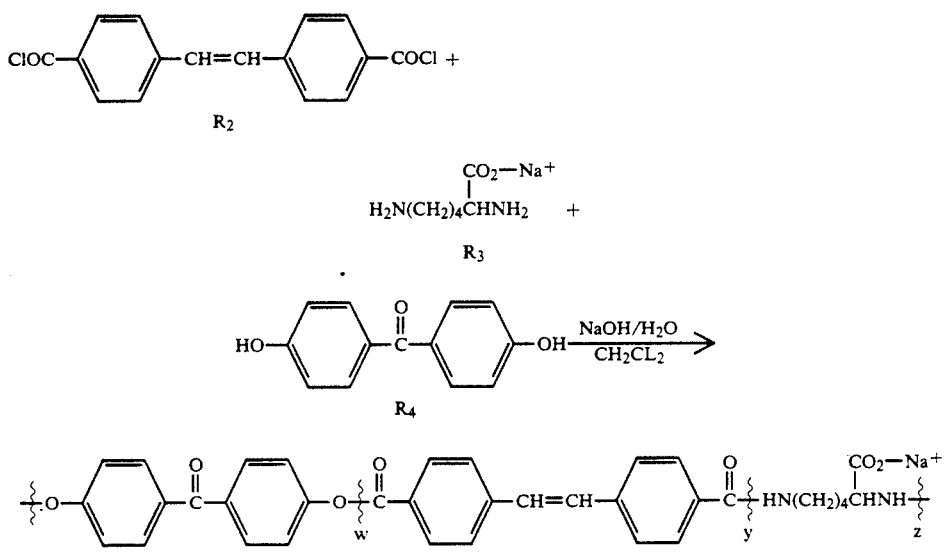

Scheme 1
w = 0.1–49.9 mol %
y = 50 mol %
z = 0.1–49.9 mol %

According to scheme 1, the hydrophilic lysine sodium salt monomer has been incorporated to facilitate polymer transfer through an aqueous medium. The UVB light-absorbing 4,4'-dihydroxybenzophenone monomer has been incorporated to absorb at its $\lambda$max ultraviolet light between 290 and 320 nm in wavelength. The UVA light-absorbing 4,4'-stilbenedicarbonyl dichloride monomer has been incorporated to absorb at its $\lambda$max ultraviolet light between 320 and 400 in wavelength. The 4,4'-dihydroxybenzophenone was obtained commercially. The 4,4'-stilbenedicarbonyl dichloride was prepared by a known route. R. Kluger et al., *J. Org. Chem.*, 55(9):2864 (1990). The lysine sodium salt was prepared in situ from commercially available lysine hydrochloride and sodium hydroxide, as described above.

Broad spectrum water dispersible polymers as shown in Scheme 1 were obtained by charging the reaction vessel with 1 eq. of 4,4'-stilbenedicarbonyl dichloride, 0.75 eq. of 4,4'-dihydroxybenzophenone, 0.25 eq. of lysine hydrochloride, and 2.25 eq. of a suitable base such as NaOH. The reaction was run interfacially using a water/chlorinated hydrocarbon solvent system. The contents of the reaction vessel were kept at 30°–35° C.

for between 16 and 20h. The resulting materials ranged in glass transition temperature (Tg) from 75 to 107° C. and absorbed at the chromophores' max UV light in the UVB (290-320 nm) and UVA (320-400 nm) range.

The chlorinated hydrocarbon cosolvent useful for synthesizing broad spectrum water dispersible polymers as shown in Scheme 1 include but are not limited to methylene chloride, chloroform, 1,2-dichloroethane, and chlorinated aromatics such as chlorobenzene or 1,1-dichlorobenzene; or mixtures thereof. Suitable bases include organic amines such as triethylamine, diethylamine, diisopropylamine, diisopropylethylamine, pyridine, and 4-dimethylaminopyridine; alkali metal hydroxides such as sodium hydroxide, lithium hydroxide, and potassium hydroxide; alkali metal carbonates such as sodium carbonate, lithium carbonate, and potassium carbonate; or mixtures thereof.

The cosolvent system may be used as 1-50% by weight of the solids content of the reaction. The ratio of water to chlorinated hydrocarbon may range from 1:10 to 10:1, preferably 1:5 to 5:1, and most preferably 2:1 to 1:2. Reaction temperatures may range from $-78°$ C. to reflux temperatures, preferably $0°$ to $50°$ C., and most preferably $25°$ to $50°$ C. The time of reaction may range from 0.25 hours (h) to 48 h, preferably 0.5 h to 24 h, and most preferably 1 h to 20 h.

4,4'-Dihydroxybenzophenone was obtained commercially. 4,4'-Stilbenedicarbonyl dichloride was synthesized from 4,4'-stilbenedicarboxylic acid and thionyl chloride according to R. Kluger, et al., *J. Org. Chem.*, 55(9):2864 (1990), and was used without further purification. 4,4'-Stilbenedicarboxylic acid was obtained commercially. Lysine sodium salt was prepared in situ by treatment of lysine hydrochloride with sodium hydroxide. $^1$H NMR spectra were recorded on a Bruker AC-200 or Varian 300 MHz Spectrometer as indicated at ambient temperature. Samples were dissolved in deuterated DMSO with tetramethylsilane as an internal standard. UV absorbance data were obtained on a Beckman DU-65 Spectrophotometer at a concentration of 0.01-0.3g UV light-absorbing polymer/liter so that the absorbance was kept between 0.3 and 1.0 absorbance units. Dimethyl sulfoxide was used as the sample and reference solvent. Extinction values ($\epsilon$) were calculated from the Beer-Lambert equation, $\epsilon = A/cl$, where $\epsilon$ = molar extinction coefficient, A = absorbance, c = molar concentration, and l = path length). Molar concentration (c) is derived from the mol % chromophore.

The following examples are intended to illustrate the invention and facilitate its understanding and are not meant to limit it in any way.

EXAMPLE 1

Synthesis of 4,4'-Stilbenedicarbonyl Dichloride

To a 500 mL round bottom flask fitted with a reflux condenser and nitrogen inlet tube was added 15.15 g (0.057 mol) 4,4'-stilbenedicarboxylic acid, 248 mL (3.39 mol) thionyl chloride, and several drops of DMF. The reaction vessel was heated to reflux temperature for 24 h. The excess thionyl chloride was distilled in vacuo at room temperature to afford 4,4'-stilbenedicarbonyl dichloride, which was used without further purification: $^1$H NMR (CD$_3$SOCD$_3$, 200 MHz) δ 7.51 (s, 2H), 7.78 (broad d, 4H), 7.87 (broad d, 4H).

EXAMPLE 2

Broad Spectrum UV Light Absorbing Water Dispersible Copolymer Containing 50% UVA Light-Absorbing Unit, 25% UVB Light-Absorbing Unit, and 25% Hydrophilic Unit To a 1000 mL round bottom flask fitted with a nitrogen inlet was added 3.28 g (81.97 mmol) NaOH followed by 100 mL water. After the NaOH completely dissolved, 100 mL methylene chloride was added followed by 3.51 g (16.93 mmol) 4,4'-dihydroxybenzophenone, 2.99 g (16.93 mmol) L-lysine HCl, and 10.00 g (32.80 mmol) 4,4'-stilbenedicarbonyl dichloride. The reaction mixture became viscous, and to it was added 35 mL water and 35 mL methylene chloride. The interfacial reaction mixture was allowed to stir at 50° C. overnight. The resulting solid was filtered, washed with 15-20 mL water, and dried in a vacuum oven to afford a UVA and UVB light-absorbing polymer. λmax (DMSO)=NA $^1$H NMR (CD$_3$SOCD$_3$, 300 MHz) δ 3.49 (broad s, —(CH$_2$CH$_2$O)$_x$—), 3.74 (m, —CO$_2$CH$_2$CH$_2$O—(CH$_2$CH$_2$O)$_x$—), 4.38 (m, —CO$_2$CH$_2$C$\overline{\text{H}}_2$O—(CH$_2$CH$_2$O)$_x$—), 6.86 (d, J=8.6 Hz, —OC$_6$H$_4$CO$\overline{\text{C}}_6$H$_4$O—), 7.48 (s, —COC$_6$H$_4$CH=CHC$_6$H$_4$CO—), 7.58 (d, J=8.6 Hz, —OC$_6$H$_4$CO$\overline{\text{C}}_6$H$_4$O—), 7.75 (d, J=8.6 Hz, —COC$_6$H$_4$CH=CHC$_6$H$_4$CO—), 7.94 (d, J=8.6 Hz, —COC$_6$$\overline{\text{H}}_4$CH=CHC$_6$H$_4$CO—).

EXAMPLE 3

Broad Spectrum UV Light-Absorbing Water-Dispersible Copolymer Containing 50% UVA Light-Absorbing Unit, 37.5% UVB Light-Absorbing Unit, and 12.5% Hydrophilic Unit To a 200 mL round bottom flask fitted with a nitrogen inlet was added 0.59 g (14.1 mmol) NaOH followed by 25 mL water. After the NaOH completely dissolved, 25 mL methylene chloride was added, followed by 1.05 g (4.92 mmol) 4,4'-dihydroxybenzophenone, 0.30 g (1.64 mmol) L=lysine - HCl, and 2.00 g (6.55 mmol) 4,4'-stilbenedicarbonyl dichloride. The reaction mixture became viscous, and to it was added 35 mL water and 35 mL methylene chloride. The interfacial reaction mixture was allowed to stir at 30°-35° C. overnight. The resulting solid was filtered, washed with 15-20 mL water, and dried in a vacuum oven to afford a UVA and UVB light-absorbing polymer: λmax (DMSO)=NA; $^1$H NMR (CD$_3$SOCD$_3$, 300 MHz) δ 3.49 (broad s, —(CH$_2$CH$_2$O)$_x$—), 3.74 (m, —CO$_2$CH$_2$C-H$_2$O—(CH$_2$CH$_2$O)$_x$—), 4.38 (m, —CO$_2$CH$_2$C-$\overline{\text{H}}_2$O—(CH$_2$C$\overline{\text{H}}_2$O)$_x$—), 6.86 (d,J=8.6 Hz, —OC$_6$H$_4$COC$_6$H$_4$O—), 7.48 (s, —COC$_6$H$_4$CH=CHC$_6$H$_4$CO—), 7.58 (d, J=8.6 Hz, —OC$_6$H$_4$COC$_6$H$_4$O—), 7.75 (d, J=8.6 Hz, —COC$_6$H$_4$CH=CHC$_6$H$_4$CO—), 7.94 (d, J=8.6 Hz, —COC$_6$$\overline{\text{H}}_4$$\overline{\text{C}}$H=CHC$_6$H$_4$CO—).

EXAMPLE 4

Broad Spectrum UV Light-Absorbing Water Dispersible Copolymer Containing 50% UVA Light-Absorbing Unit. 45% UVB Light-Absorbing Unit, and 5% Hydrophilic Unit To a 200 mL round bottom flask fitted with a nitrogen inlet was added 0.55 g (13.77 mmol) NaOH followed by 25 mL water. After the NaOH completely dissolved, 25 mL methylene chloride was added, followed by 1.26 g (5.90 mmol) 4,4'-dihydroxybenzophenone, 0.12 g (0.66 mmol) L-lysine - HCl, and 2.00 g (6.55 mmol) 4,4'-stilbenedicarbonyl dichloride. The interfacial reaction mixture was allowed to stir at 30-35° C. overnight. The resulting solid was filtered, washed with 15-20 mL water, and dried in a vacuum oven to afford a UVA and UVB light-absorbing polymer: $\lambda$max (DMSO)=NA; $\epsilon$=14,000, 15,700, 11,300; $^1$H NMR (CD$_3$SOCD$_3$, 300 MHz) $\delta$ 3.49 (broad s, —CH$_2$CH$_2$O)$_x$—), 3.74 (m, —CO$_2$CH$_2$CH$_2$O——(CH$_2$CH$_2$O)$_x$—), 4.38 (m, —C$_2$CH$_2$CH$_2$O—(CH$_2$CH$_2$O)$_x$—), 6.86 (d, J=8.6 Hz, —OC$_6$H$_4$COC$_6$H$_4$O—), 7.48 (s, —COC$_6$H$_4$CH=CHC$_6$H$_4$CO—), 7.58 (d, J=8.6 Hz, —OC$_6$H$_4$COC$_6$H$_4$O—), 7.75 (d, J=8.6 Hz, —COC$_6$H$_4$CH=CHC$_6$H$_4$CO—), 7.94 (d, J=8.6 Hz, —COC$_6$H$_4$CH=CHC$_6$H$_4$CO—).

EXAMPLES 5-9

Use of copolymers of the Invention in Heavy Duty Liquid (HDL) Compositions.

| Ingredient | wt. % | | | | |
|---|---|---|---|---|---|
|  | 5 | 6 | 7 | 8 | 9 |
| Sodium C$_{11}$-C$_{15}$ Alkyl Benzene Sulfonate | 10.0 | 17.0 | 26.0 | 15.0 | 11.6 |
| Sodium Alkyl Ethoxy Sulfate (2) | 6.0 | — | — | — | 8.2 |
| Alcohol Ethoxylate (1) | 8.0 | 7.0 | 12.0 | 5.0 | 4.2 |
| Sodium Citrate | 7.0 | 7.0 | 10.0 | — | 5.0 |
| Sodium Salt of C$_{12}$-C$_{18}$ Fatty Acid | — | — | — | — | 3.6 |
| Sodium Tartrate Mono and Disuccinate | — | — | — | — | 3.1 |
| Monoethanolamine | 2.0 | 2.0 | 2.0 | — | — |
| Triethanolamine | 2.0 | 2.0 | 2.0 | — | — |
| Sodium Silicate | — | — | — | 2.5 | — |
| Savinase | 0.75 | — | 0.75 | — | 0.4 |
| Sodium Borate | 3.5 | — | 3.5 | — | — |
| Sodium Formate | — | — | — | — | 1.2 |
| Glycerol | — | — | 5.0 | — | — |
| Propylene Glycol | 4.0 | — | — | — | 4.5 |
| Sodium Xylene Sulfonate | 3.0 | 3.0 | — | 1.0 | 2.3 |
| Ethanol | — | — | — | 1.0 | — |
| Tinopal UNPA | 0.25 | 0.25 | 0.2 | 0.1 | 0.2 |
| UV Absorbing Polymer of Invention | 0.05 to 15.0 | | | | |
| Water | to 100.0 | | | | |

(1) C$_{12}$ to C$_{15}$ alcohol condensed with 9 mole ethylene oxide
(2) C$_{12}$ to C$_{15}$ alcohol condensed with 3 mole ethylene oxide and sulfated.

EXAMPLES 10-14

Use of copolymers of the Invention in Powdered Detergent Compositions.

| Ingredient | wt. % | | | | |
|---|---|---|---|---|---|
|  | 10 | 11 | 12 | 13 | 14 |
| Sodium C$_{11}$-C$_{12}$ Alkyl Benzene Sulfonate | 11.0 | 11.5 | 18.0 | 11.0 | 15.0 |
| Sodium C$_{12}$-C$_{15}$ Alkyl Ethoxy Sulfate (2) | — | 5.5 | — | — | — |
| Sodium C$_{12}$-C$_{15}$ Alkyl Sulfate | 10.0 | — | — | 9.0 | 5.0 |
| Alcohol Ethoxylate (1) | — | 3.0 | — | 2.0 | 3.0 |
| Sodium Salt of C$_{12}$-C$_{18}$ Fatty Acid | 1.0 | — | — | — | 1.0 |
| Sodium Tripolyphosphate | — | — | — | — | 25.0 |
| Sodium Aluminosilicate | 25.0 | 15.0 | 20.0 | 10.0 | — |
| Sodium Silicate | 3.0 | 20.0 | 5.0 | 15.0 | 15.0 |
| Sodium Carbonate | 18.0 | 18.0 | 15.0 | 30.0 | 20.0 |
| Savinase | 0.5 | 0.5 | 0.5 | 0.5 | 1.0 |
| Tinopal AMS | 0.15 | 0.2 | 0.25 | 0.15 | 0.15 |
| UV Absorbing Polymer of Invention | 0.05 to 15.0 | | | | |
| Sodium Sulfate | to 100.0 | | | | |

(1) C$_{12}$ to C$_{15}$ alcohol condensed with 9 mole ethylene oxide
(2) C$_{12}$ to C$_{15}$ alcohol condensed with 3 mole ethylene oxide and sulfated.

EXAMPLES 15-17

Use of copolymers of the Invention in Fabric Softener Compositions.

| Ingredient | wt. % | | |
|---|---|---|---|
|  | 15 | 16 | 17 |
| Dimethyldialkyl ammonium chloride | 3.2 | 6.5 | 6.25 |
| Trimethylalkyl ammonium chloride | 0.6 | 0.9 | — |
| Alkyl amidoethyl alkyl imidazoline | 3.3 | 16.0 | — |
| Polydimethyl siloxane | 0.1 | 0.5 | — |
| Ethanol | 0.7 | 1.4 | — |
| Calcium chloride | 0.1 | 0.3 | 0.1 |
| UV Absorbing Polymer of Invention | 0.05 to 15.0 | | |
| Water | to 100.00 | | |

EXAMPLE 18

Preparation of Sunscreen Compositions

Three premixes were prepared as shown below:

| Premix A | |
|---|---|
| Finsolv TN* | 2.5 |
| Stearic Acid | 1.0 |
| Amphosol** | 0.75 |
| Cetyl Alcohol | 0.375 |
| UVA UVB Polymer | 2.5 |
| Premix B | |
| Deionized Water (DI) | 12.48 |
| Triethonolamine | 0.25 |
| Carbopol 980*** | 0.035 |
| Premix C | |
| DI Water | 5.0 |
| Methyl Paraban | 0.075 |
| Propyl Paraban | 0.025 |

Premix A - Finsolv TN was heated to 80° C. and stearic acid amphosol. and cetyl alcohol were added. The ingredients were mixed until clear and homogeneous. UV polymer was added. The premix was maintained at 80° C.
Premix B - Water was heated to 80° C. and triethanoline and Carbopol were added. Ingredients were mixed until clear gel formed and the premix was maintained at 80° C.
Premix C - Water was heated to 40° C. and methyl paraban and propyl paraban were added.
Premix A was added to premix B and allowed to cool to 40° C. under high shear, then premix C was added and allowed to cool to room temperature.
*Finsolv TN = Benzoic Acid Ester of C$_{12}$-C$_{15}$ alcohol
***Carbopol 980 = Poly (acrylic acid)
**Amphosol = Cocamidobetaine

We claim:
1. A copolymer having the formula:

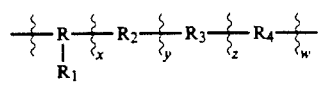

wherein:
R is a difunctional aryl or alkyl group or a difunctional straight or branched alkyl chain containing 4 to 16 carbon atoms;
R$_1$ is hydrogen or an aliphatic group having 1 to 20 carbons, an aryl, an alkaryl, a secondary amine, an alkali metal sulfonate, an alkali metal carboxylate, an alkyl ether, or a halogen atom;

$R_2$ is a difunctional moiety absorbing UVA light at λmax;

$R_3$ is a charged moiety selected from the group consisting of a carboxylate salt, a sulfonate salt, and a quaternary ammonium derivative;

$R_4$ is a difunctional moiety absorbing UVB light at λmax;

x is selected such that the hydrophobe is present at 0 to 49.9 mol % of the polymer;

y is selected such that the $R_2$ group is present at 0 to 99.9 mol % of the polymer;

z is selected such that the $R_3$ group is present at 0.5 to 49.9 mol % of the polymer; and w is selected such that the $R_4$ group is present at 0 to 99.9 mol % of the polymer;

wherein y must be greater than 0 if w is 0 and w must be greater than 0 if y is 0.

2. A copolymer according to claim 1 wherein said carboxylate salt is a hydroxy-, phenylhydroxy-, thio-, or diaminoacid salt selected from the group consisting of cysteine acid salt, hydroxylysine acid salt, hydroxyproline acid salt, lysine acid salt, serine acid salt, threonine acid salt, and tyrosine acid salt.

3. A copolymer according to claim 1 wherein $R_3$ is —HN(CH$_2$)$_4$CH(CO$_2$—Na$^+$)NH—.

4. A copolymer according to claim 1 wherein said quaternary ammonium derivative is 2,3-dihydroxypropyltrimethylammonium chloride.

5. A copolymer according to claim 1 wherein $R_3$ is —OCH$_2$CH(CH$_2$NMe$_3$+Cl$^-$)O—.

6. A copolymer according to claim 1 wherein $R_4$ is

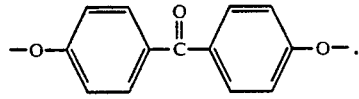

7. A copolymer according to claim 1 wherein $R_2$ is

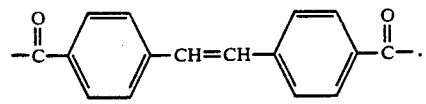

8. A copolymer according to claim 1, wherein $R_4$ is

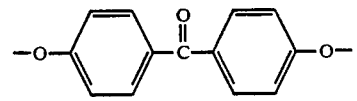

$R_3$ is —HN(CH$_2$)$_4$CH—(CO$_2$—Na$^+$)NH—; and $R_2$ is

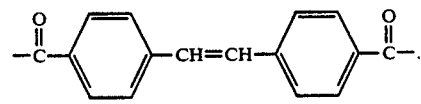

9. A copolymer according to claim 1 prepared by polymerizing a mixture of 4,4'-stilbenedicarbonyl dichloride, 4,4'-dihydroxybenzophenone, and lysine hydrochloride.

10. A copolymer according to claim 1 wherein $R_2$ is

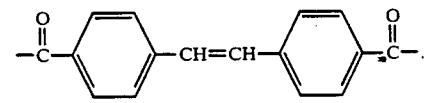

$R_3$ is —OCH$_2$CH(CH$_2$NMe$_3$+Cl$^-$)O—; and $R_4$ is

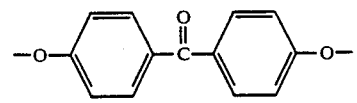

11. A copolymer according to claim 1 prepared by polymerizing a mixture of 4,4'-stilbenedicarbonyl dichloride, 4,4'-dihydroxybenzophenone, and 2,3-dihydroxypropyltrimethylammonium chloride.

* * * * *